United States Patent
Warner et al.

(10) Patent No.: US 6,562,588 B2
(45) Date of Patent: *May 13, 2003

(54) SIALIDASE AND RECOMBINANT CELL LINES

(75) Inventors: Thomas G. Warner, San Carlos, CA (US); Mary B. Sliwkowski, San Carlos, CA (US)

(73) Assignee: Genentech, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/871,076

(22) Filed: Jun. 9, 1997

(65) Prior Publication Data

US 2002/0076791 A1 Jun. 20, 2002

Related U.S. Application Data

(63) Continuation of application No. 08/711,374, filed on Sep. 5, 1996, now abandoned, which is a continuation of application No. 08/536,013, filed on Sep. 29, 1995, now abandoned, which is a continuation of application No. 08/383,551, filed on Jan. 31, 1995, now abandoned, which is a continuation of application No. 08/062,586, filed on May 17, 1993, now abandoned.

(51) Int. Cl.$^7$ ................................................ C12P 21/02
(52) U.S. Cl. ........................................ 435/69.1; 435/358
(58) Field of Search ............................. 435/69.1, 320.1, 435/325, 172.3, 358; 536/23.2

(56) References Cited

U.S. PATENT DOCUMENTS

| | | | |
|---|---|---|---|
| 4,912,040 A | * 3/1990 | Kaufman et al. | ........... 435/69.6 |
| 4,912,090 A | 3/1990 | Kaufman et al. | |
| 5,047,335 A | * 9/1991 | Paulson et al. | ............ 435/69.1 |
| 5,075,218 A | * 12/1991 | Vette et al. | ................. 435/7.23 |

FOREIGN PATENT DOCUMENTS

| | | | |
|---|---|---|---|
| WO | WO 93/10260 | 5/1993 | ............ C12Q/1/34 |

OTHER PUBLICATIONS

Sambrook et al., *Molecular Cloning: A Laboratory Manual*, 2nd ed., Cold Spring Harbor Lab. Press, 1989, pp. 12.2–12.29.*
Miyagi et al., *J. Biochem.*, vol. 107, 1990, pp. 794–798.*
Miyagi et al., *Tohoku J. Exp. Med.*, vol. 168, 1992, pp. 223–229.*
Hoyer et al., *Mol. Microbiology*, vol. 6, 1992, pp. 873–884.*
Mueller et al., *PNAS*, vol. 83, 1986, pp. 1817–1821.*
Goochee, C. F. et al., "Potential for Degradation of Glycoprotein Oligosaccharides by Extracellular Glycosidases", *J. Cell Biochem.*, 16(D), P 209, p. 154 (1992).

Russo, T. A. et al., "Cloning and Expression of the *Bacteroides fragilis* TAL 2480 Neuraminidase Gene nanH, in *Escherichia coli*", *Journal of Bacteriology*, vol. 172, No. 5, pp. 2594–2600 (May 1990).
Air et al., "The Neuraminidase of Influenza Virus" *Proteins: Struct. Func. Genet.* 6(341) :341–356 (1989).
Burger et al., "Stable expression of rabies virus glycoprotein in Chinese hamster ovary cells"*J. Gen. Virol.* 72:359–367 (1991).
Ferrari et al., "Cloning and Expression of a Soluble Sialidase from Chinese Hamster Ovary Cells: Sequence Alignment Similarities to Bacterial Sialidases" *Glycobiology* 4(3) : 367–373 (Jun. 1994).
Godoy et al., "A Role for *Bacteroides fragilis* Neuraminidase in Bacterial Growth in Two Model Systems" *Infect. Immun.* 61 (10) :4415–4426 (Oct. 1993).
Gramer et al., "Potential for Degradation of Glycoprotein Oligosaccharides by Extracellular Glycosidases"*Am. Chem. Soc.* (Abstract, 203rd Meeting, San Francisco, CA) PT 1:BIOT–71 (Apr. 5, 1992).
Miyagi et al., "Immunological Discrimination of Intralysosomal, Cytosolic, and Two Membrane Sialidases Present in Rat Tissues" *J. Biochem.* 107:794–798 (1990).
Miyagi et al., "Multiple Forms of Mammalian Sialidase: Altered Expression in Carcinogenesis" *Tohoku J. Exp. Med.* 168:223–229 (1992).
Miyagi et al., "Purification and Characterization of Cystosolic Sialidase from Rat Liver" *J. of Biol. Chem.* 260 (11) : 6710–6716 (1985).
Sambrook et al. *Molecular Cloning: A Laboratory Manual*, 2nd edition, Cold Spring Harbor Lab. Press pp. 12.2–12.29 (1989).
Schengrund et al., "Ecto–Ganglioside–Sialidase Activity of Herpes Simplex Virus–Transformed Hamster Embryo Fibroblasts" *Journal of Cell Biology* 70:555–561 (1976).
Sheehan et al., "A Single Amino Acid Substitution in the Hemagglutinin–neuraminidase of Newcastle Disease Virus Results in a Protein Deficient in Both Functions" *Virology* 189 (2) :778–781 (Aug. 1992).
Tulsiani et al., "Studies on the Soluble and Lysosomal Neuraminidases of Rat Liver" *Journal of Biological Chemistry* 245 (7) :1821–1827 (1970).
Warner et al., "Isolation and Properties of a Soluble Sialidase from the Culture Fluid of Chinese Hamster Ovary Cells" *Glycobiology* 3 (5) :455–463 (Oct. 1993).

(List continued on next page.)

Primary Examiner—James Ketter
(74) Attorney, Agent, or Firm—Merchant & Gould P.C.

(57) ABSTRACT

A recombinant cell line has a constitutive sialidase whose functional expression is disrupted, for example by homologous recombination or using antisense RNA. Sialidase is purified from cell culture fluid of Chinese hamster ovary cells. Nucleic acid encoding sialidase is obtained using an oligonucleotide probe designed using amino acid sequence data on the sialidase.

3 Claims, 5 Drawing Sheets

OTHER PUBLICATIONS

Waxham et al., "Identification of Amino Acids Involved in the Sialidase Activity of the Mumps Virus Hemagglutinin––neuraminidase Protein" *Virology* 167 (1) :226–232 (Nov. 1988).

Air, G. M., et al., "The Neuraminidase of Influenza Virus", *PROTEINS: Structure, Function, and Genetics* 6:341–356 (1989).

Miyagi, T., et al., "Purification and Characterization of Cytosolic Sialidase from Rat Liver", *The Journal of Biological Chemistry* 260 (11) :6710–6716 (1985).

Schengrund, C. L., et al., "Ecto–Ganglioside–Sialidase Activity of Herpes Simplex Virus–Transformed Hamster Embryo Fibroblasts", *The Journal of Cell Biology* 70:555–561 (1976).

Tulsiani, D. R. P., et al., "Studies on the Soluble and Lysosomal Neuraminidases of Rat Liver", *The Journal of Biological Chemistry* 245 (7) :1821–1827 (1970).

Stanley, P., "CHO Mutants Available for Glycosylation Engineering" (Abstract from conference on Glycotechnology held in San Francisco May 17–19) (1993).

* cited by examiner

1. VVYLNAR

2. VQAQSPNSGLDFQDN

3. ETLFQTGDYAYR

4. IPALIYLSK

5. ADALDVWLLYTHPTDSR

6. ETLFQTGDYAYRIPALIYLSK

7. LGHFVSQNSLE

8. VGPGHCLQLRNTAGSLLVPAYAYRKQPPIHXPAPSAFXFLSHD

9. HHQLQTGVNVTRLCHITSTDHGKTWSAVQDLTDTTIGSSDQDXAXFGVGPF

10. TDEHADLFVLRRGSYNADTHQVQWQAEEVVT

11. CRVQAQSPNSGLDFQDN

FIG. 8

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Val Val Tyr Leu Asn Ala Arg
1               5

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Val Gln Ala Gln Ser Pro Asn Ser Gly Leu Asp Phe Gln Asp Asn
1               5                   10                  15

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Glu Thr Leu Phe Gln Thr Gly Asp Tyr Ala Tyr Arg
1               5                   10

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ile Pro Ala Leu Ile Tyr Leu Ser Lys
1               5

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ala Asp Ala Leu Asp Val Trp Leu Leu Tyr Thr His Pro Thr Asp Ser
1               5                   10                  15
Arg (2) INFORMATION FOR SEQ ID NO:6:

(i) SEQUENCE CHARACTERISTICS:
        (A) LENGTH: 21 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Glu Thr Leu Phe Gln Thr Gly Asp Tyr Ala Tyr Arg Ile Pro Ala Leu
1               5                   10                  15

Ile Tyr Leu Ser Lys
            20

(2) INFORMATION FOR SEQ ID NO:7:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Leu Gly His Phe Val Ser Gln Asn Ser Leu Glu
1               5                   10

(2) INFORMATION FOR SEQ ID NO:8:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Val Gly Pro Gly His Cys Leu Gln Leu Arg Asn Thr Ala Gly Ser Leu
1               5                   10                  15

Leu Val Pro Ala Tyr Ala Tyr Arg Lys Gln Pro Pro Ile His Xaa Pro
            20                  25                  30

Ala Pro Ser Ala Phe Xaa Phe Leu Ser His Asp
        35                  40

(2) INFORMATION FOR SEQ ID NO:9:

(i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

His His Gln Leu Gln Thr Gly Val Asn Val Thr Arg Leu Cys His Ile
1               5                   10                  15

Thr Ser Thr Asp His Gly Lys Thr Trp Ser Ala Val Gln Asp Leu Thr
            20                  25                  30

Asp Thr Thr Ile Gly Ser Ser Asp Gln Asp Xaa Ala Xaa Phe Gly Val
        35                  40                  45

Gly Pro Phe
      50

(2) INFORMATION FOR SEQ ID NO:10:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Thr Asp Glu His Ala Asp Leu Phe Val Leu Arg Arg Gly Ser Tyr Asn
1               5                   10                  15

Ala Asp Thr His Gln Val Gln Trp Gln Ala Glu Glu Val Val Thr
            20                  25                  30

(2) INFORMATION FOR SEQ ID NO:11:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Cys Arg Val Gln Ala Gln Ser Pro Asn Ser Gly Leu Asp Phe Gln Asp
1               5                   10                  15

Asn

SIALIDASE AND RECOMBINANT CELL LINES

This is a continuation of applications Ser. No. 08/711,374 filed Sep. 5, 1996, now abandoned which is a continuation of Ser. No. 08/536,013 filed on Sep. 29, 1995, now abandoned, which is a continuation of Ser. No. 08/383,551 filed on Jan. 31, 1995, now abandoned, which is a continuation of Ser. No. 08/062,586 filed on May 17, 1993, now abandoned, which applications are incorporated herein by reference and to which application(s) priority is claimed under 35 USC § 120.

FIELD OF THE INVENTION

This invention relates to sialidase activity, in particular isolated sialidase enzyme and recombinant cell lines having modified sialidase activity.

BACKGROUND OF THE INVENTION

Sialidases are a family of glycohydrolytic enzymes which cleave sialic acid residues from the oligosaccharide components of glycoproteins and glycolipids. Viral and bacterial enzymes have been studied, for example the influenza sialidases in particular (Air, G. M. and Laver, W. G. (1989) *Proteins: Struct. Func. Genet.*, 6:341), but mammalian sialidases have not been well characterized. For the most part, studies of mammalian sialidases have been confined to investigation of substrate specificities and kinetic analysis using partially purified preparations, although a sialidase from rat liver and muscle has been purified to homogeneity (Miyagi, T. and Tsuiki, S. (1985) *J. Biol. Chem.*, 260:6710). Sialidases have been identified in a number of cellular organelles: the plasma membrane (Schengrund, C., Rosenberg, A., and Repman, M. A. (1976) *J. Cell. Biol.*, 70:555), the lysosomes and the cytosol (Tulsiani, D. R. P., and Carubelli, R., (1970) *J. Biol. Chem.*, 245:1821).

Glycoproteins are often produced by expression of encoding genes in recombinant host cells in vitro, the cells having the normal enzyme components of cellular glycosylation machinery. Sialic acid in the oligosaccharide component of a glycoprotein is involved in mediation of clearance from the serum and affects the physical, chemical and immunogenic properties of the protein molecule. It is therefore important to maintain the sialic acid content of glycoproteins, particularly of those proteins intended for use as therapeutics.

SUMMARY OF THE INVENTION

The present invention is based on modification in a recombinant cell line of the constitutive expression of genes which encode enzymes which are involved in the destruction or production of the oligosaccharide portions of glycoproteins. In particular, the modification to the recombinant cell line may be such as to ensure that the gene or genes of interest are not functionally expressed. Of particular interest is a sialidase gene within a recombinant cell line, especially a gene encoding a cytosolic sialidase. Example cell lines are those derived from Chinese hamster ovaries and human embryonic kidneys.

In the recombinant cell line functional gene expression may be disrupted by mutation, addition or deletion of one or more nucleotides. Such mutation, addition or deletion may be by any of the methods known to the person skilled in the art, for instance homologous recombination between the genomic gene and a differing but largely homologous nucleic acid sequence introduced into the cells. The gene may be deleted altogether.

The gene may be not functionally expressed by virtue of disruption of the gene function by regulation of its transcription or translation, eg using antisense RNA.

The present invention also provides a substantially homogeneous sialidase which can be obtained from cell culture fluid of a Chinese hamster ovary cell line. Characteristics of such a sialidase are described and discussed infra.

It also provides an oligonucleotide probe which is useful in obtaining a sialidase-encoding gene and a nucleic acid sequence obtained by a process comprising hybridizing the probe with nucleic acid in a mammalian DNA library to form hybrids which can be isolated. The nucleic acid may be used for expression of sialidase. It may be modified in all manner of ways, eg by mutation, addition or deletion of one or more nucleotides, amplification, cleavage and tailoring.

In a preferred embodiment of the present invention a sialidase gene of a cell line is disrupted so that it is not functionally expressed, the level of functional sialidase produced by the cells being such that sialic acid residues in the carbohydrate side-chains of glycoprotein produced by the cells are not cleaved, or are not cleaved to an extent which affects the function of the glycoprotein. Such cells are useful as host cells for the expression of recombinant glycoproteins from nucleic acid transformed into the cells under appropriate conditions. Glycoproteins produced by expression of encoding nucleic acid introduced into these cells should have intact, functional carbohydrate side chains.

DETAILED DESCRIPTION OF THE INVENTION

Definitions

Recombinant Cell Line

This expression refers to cells established in ex vivo culture and which have some genetic modification from the original parent cells from which they are derived. Such genetic modification may be the result of introduction of a heterologous gene for expression of the gene product, or it may be by the introduction of a gene, possibly with promoter elements, for production within the cells of antisense RNA to regulate expression of another gene. Equally, the genetic modification may be the result of mutation, addition or deletion of one or more nucleotides of a gene or even deletion of a gene altogether, by any mechanism. Cells of a recombinant cell line used in the production of a desired protein product have the means for glycosylating proteins by addition of oligosaccharide side chains. Such cells also have the capability to remove and/or modify enzymatically part or all of the oligosaccharide side chains of glycoproteins.

Functional Expression, and Grammatically Related Terms

Functional expression of a gene refers to production of the protein product encoded by the gene in a form or to the extent required for the product to perform its normal function within the cell environment. Thus, a gene encoding an enzyme involved in protein glycosylation, or deglycosylation, is functionally expressed when enough of the enzyme is produced in a working form to glycosylate, or deglycosylate, at a normal level protein produced in the cell. Functional expression of a gene may be disrupted by modification of the nucleotide sequence of the gene so that protein product of the gene is defective in its function, or by deletion or modification of part or all of promoter sequences associated with the gene and involved in transcription of the gene, or by deletion of the gene itself from the genome of the cell, or by interference with translation of mRNA transcribed from the gene eg interference by antisense RNA, or by any combination of any of these with each other or with any other means known to the person skilled in the art for disrupting gene function.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its insert (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell" and "transformed" refer to the introduction of DNA into a cell. The cell is termed a "host cell", and it may be a prokaryotic or a eukaryotic cell. Typical prokaryotic host cells include various strains of E. coli. Typical eukaryotic host cells are mammalian, such as Chinese hamster ovary cells or human embryonic kidney 293 cells. The introduced DNA is usually in the form of a vector containing an inserted piece of DNA. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. Restriction enzymes are commercially available and are used according to the instructions supplied by the manufacturers. Restriction enzymes are designated by abbreviations composed of a capital letter followed by two or three lower case letters representing the microorganism from which each restriction enzyme was obtained. These letters are followed by one or more Roman numerals that identify the particular enzyme. In general, about 1 $\mu$g of plasmid or DNA fragment is used with about 2 unites of enzyme in about 20 $\mu$l of buffer solution. The appropriate buffer, substrate concentration, incubation temperature, and incubation time for each enzyme is specified by the manufacturer. After incubation, the enzyme and other contaminants are removed from the DNA by extraction with a solution of phenol-chloroform, and the digested DNA is recovered from the aqueous fraction by precipitation with ethanol. Digestion with a restriction enzyme may be followed by treatment with bacterial alkaline phosphatase or calf intestinal alkaline phosphatase. This prevents the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. These procedures and reagents for dephosphorylation are described in sections 1.60–1.61 and sections 3.38–3.39 of Sambrook et al., (*Molecular Cloning: A Laboratory Manual*, second edition, Cold Spring Harbor Laboratory Press, New York [1989]).

"Recovery" or "isolation" of a given fragment of DNA from a restriction digest means separation of the resulting DNA fragment on a polyacrylamide or an agarose cell by electrophoresis, identification of the fragment of interest by comparison of its mobility versus that of marker DNA fragments of known molecular weight, removal of the gel section containing the desired fragment, and separation of the gel from DNA. This procedure is known generally. For example see R. Lawn et al., 1981, *Nucleic Acids Res.*, 9:6103, and D. Goeddel et al., 1980, *Nucleic Acids Res.*, 8:4057.

"Southern Analysis" or "Southern blotting" is a method by which the presence of DNA sequences in a digest or DNA-containing composition is confirmed by hybridization to a known, labelled oligonucleotide or DNA fragment. Southern analysis refers to the separation of digested DNA on an agarose gel, denaturation of the DNA, and transfer of the DNA from the gel to a nitrocellulose or nylon membrane using methods originally described by Southern (*J. Mol. Biol.*, 98:503 [1975]) and modified as described in sections 9.31–9.57 of Sambrook et al., supra.

"Transformation" means introducing DNA into an organism so that the DNA is replicable, either as an extrachromosomal element or chromosomal integrant. The method used for transformation depends on whether the host cell is a eukaryote or a prokaryote. A preferred method used to transform prokaryotes is the calcium chloride method as described in section 1.82 of Sambrook et al., supra. Eukaryotes may be transformed using the calcium phosphate method as described in sections 16.32–16.37 of Sambrook et al., supra.

"Ligation" refers to the process of forming phosphodiester bonds between two double stranded DNA fragments using the enzyme ligase in a suitable buffer that also contains ATP.

"Oligonucleotide" refers to short length single or double stranded sequences of deoxyribonucleotides linked via phosphodiester bonds. The oligonucleotides may be chemically synthesized by known methods and purified on polyacrylamide gels.

Abbreviations

Neu5Ac2en, 5-acetamide-2,6-anhydro-3,5-dideoxy-D-glycero-D-galacto-non-2-enonic acid; 9-azido-Neu5Ac2en, 5-acetamido-2,6-anhydro-9-azido-3,5,9-trideoxy-D-glycero-D-galacto-non-2-enonic acid; 9-PANP-Neu5Ac2en, 9-S-(4'-azido-2'-nitro-phenyl)-5-acetamido-2,6 anhydro-9-thio-2,5,9-trideoxy-D-glycero-D-galacto-non-2-enonic acid; 4-MU-Neu5Ac, (4-methylumbelliferyl-5-acetamido-3,5-dideoxy- D-glycero-$\alpha$-D-galacto-nonulopyranosid)onic acid; HPLC, high performance liquid chromatography; SDS, sodium dodecyl sulfate; CHO, Chinese hamster ovary; EDTA, ethylene diamine tetraacetic acid; DEAE; diethylaminoethyl-; $G_{M1}$, ||$^3$NeuAc-GgOse$_4$Cer; $G_{M2}$, ||$^3$NeuAc-GgOse$_3$Cer; $G_{M3}$, ||NeuAc-LacCer; $G_{D1a}$, IV$^3$NeuAc, ||$^3$NeuAc-GgOse$_4$Cer; $G_{D1b}$, ||$^3$(NeuAc)$_2$-GgOse$_4$Cer; $G_{T1b}$, IV$^3$NeuAc, ||$^3$(NeuAc)$_2$-GgOse$_4$Cer.

Amino acids are designated thus:

| Asp | D | aspartic acid | Ile | I | isoleucine |
|---|---|---|---|---|---|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

BRIEF DESCRIPTION OF THE DRAWINGS

FIG. 8: Shows the amino acid sequences of peptides (SEQ ID NOS: 1–11) obtained tryptic digestion of the sialidase.

Figure 1:
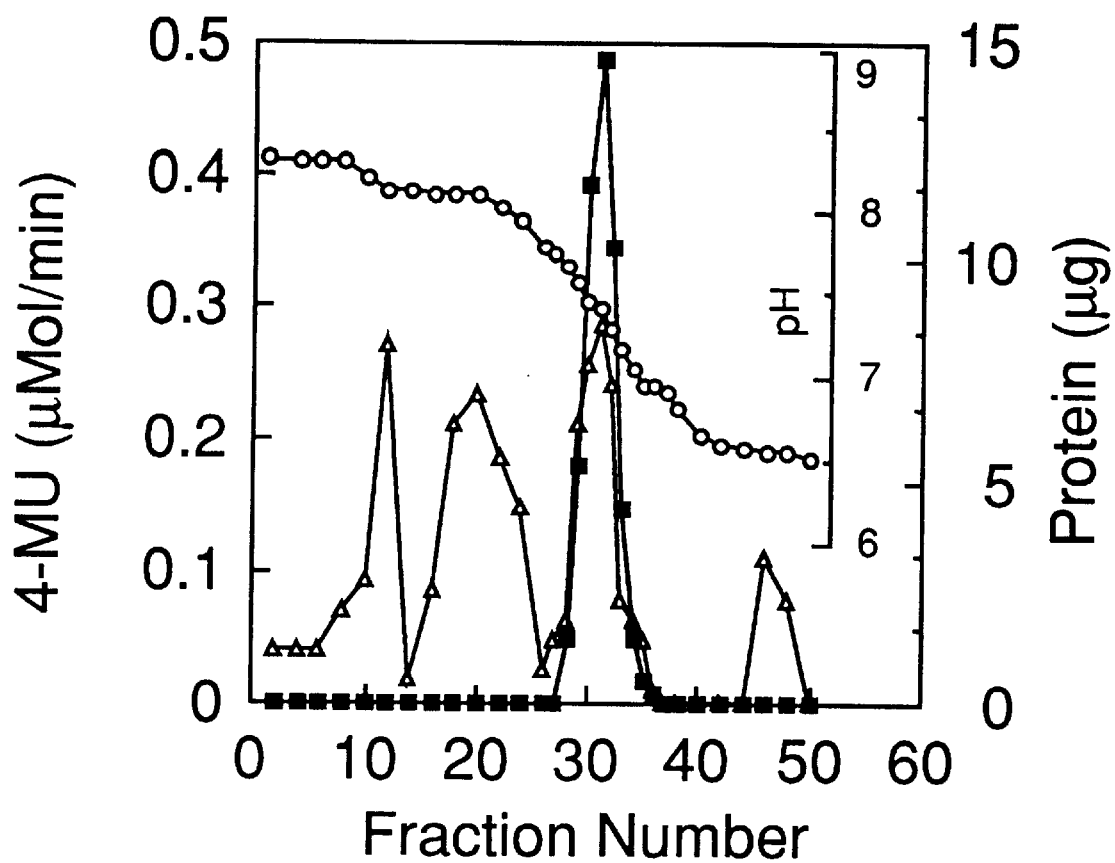
FIG. 1: Chromatofocusing elution profile of CHO cell sialidase on DEAE Sepharose. The column was eluted with Polybuffer 96 as described in Methods, o=pH of each fraction. The location of the enzyme was determined by assay using 4-MU-Neu5Ac as substrate ■=enzyme activity. Protein content (Δ) of each fraction was determined by colorometric assay.

The sialidase provided by the present invention can be used and manipulated in many ways.

Digestion of the protein with a proteolytic enzyme such as trypsin, for instance, provides relatively short polypeptides which can be sequenced using standard techniques. Amino acid sequence knowledge enables construction of oligonucleotide probes for the underlying encoding gene. Various approaches for probing for a gene are known to the person skilled in the art.

Illustrative procedures are the "mixed pool" approach of Wallace et al, Nucleic Acid Res, 6, 3543 (1979), wherein a complete set of all possible nucleotide sequences encoding a short portion of the protein is used, and the "long probe" technique of Ullrich et al, The EMBO Journal 3, no. 2, 361–364, (1984), also U.S. Ser. No. 07/841,868 (European Patent application no. 84303784.7. In the Wallace technique, one of the set of probes must have a sequence complementary to the underlying DNA sequence. The preferred Ullrich technique uses a single probe of greater than about 30 nucleotides in length which can be synthesized on the basis of the amino acid information without regard to the degeneracy of the genetic code.

The entire sialidase protein may be sequenced and the information used in the design and synthesis of oligonucleotide probes. Oligonucleotides are readily synthesized using techniques well known in the art, such as are described by Crea et al, Proc. Nat'l. Acad. Sci. USA 75, 5765 (1978) or Kunkel et al, Methods in Enzymol. 154, 367–382 (1987).

Oligonucleotide probing may be used to obtain the sialidase gene from a genomic library or a cDNA library, constructed using techniques known in the art eg as described by Maniatis et al., Molecular Cloning—A Laboratory Manual, 1982, Cold Spring Harbor Laboratory.

The DNA sequence encoding the sialidase is useful for production of the protein using recombinant DNA technology, also mutants which may have altered biological activity. Techniques for creating mutants may be also be used to produce a modified sialidase gene which will not be functionally expressed. Such a modified gene may be used in the creation of a recombinant cell line with a sialidase gene which is not functionally expressed, eg by a process involving homologous recombination, as discussed infra.

1. Simple Deletions and Insertions

Restriction endonuclease digestion of DNA followed by ligation may be used to generate deletions, as described in section 15.3 of Sambrook et al. (*Molecular Cloning: A Laboratory Manual*, second edition, Cold Spring Harbor Laboratory Press, New York [1989]). To use this method, it is preferable that the foreign DNA De inserted into a plasmid vector. A restriction map of both the foreign (inserted) DNA and the vector DNA must be available, or the sequence of the foreign DNA and the vector DNA must be known. The foreign DNA must have unique restriction sites that are not present in the vector. Deletions are then made in the foreign DNA by digesting it between these unique restriction sites, using the appropriate restriction endonucleases under conditions suggested by the manufacturer of the enzymes. If the restriction enzymes used create blunt ends or compatible ends, the ends can be directly ligated together using a ligase such as bacteriophage T4 DNA ligase and incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill-in the overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase.

A similar strategy may be used to construct insertion variants, as described in section 15.3 of Sambrook et al., supra. After digestion of the foreign DNA at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible.

2. Oligonucleotide-Mediated Mutagenesis

Oligonucleotide-directed mutagenesis may also be used to prepare conveniently the substitution deletion and insertion variants of this invention. This technique is well known in the art as described by Adelman et al. (*DNA*, 2:183 [1983]).

Generally, oligonucleotides of at least 25 nucleotides in length are used to insert, delete or substitute two or more nucleotides in the molecule. An optimal oligonucleotide will have 12 to 15 perfectly matched nucleotides on either side of the nucleotides coding for the mutation. This ensures that the oligonucleotide will hybridize properly to the single-stranded DNA template molecule. The oligonucleotides are readily synthesized using techniques well known in the art such as that described by Crea et al. (*Proc. Nat'l. Acad. Sci. USA*, 75:5765 [1978]).

The DNA template molecule is the single-stranded form of the vector with its wild-type cDNA insert. The single-stranded template can only be generated by those vectors that are either derived from bacteriophage M13 vectors (the commercially available M13mp18 and M13mp19 vectors are suitable), or those vectors that contain a single-stranded phage origin of replication as described by Veira et al. (*Meth. Enzymol.*, 153:3 [1987]). Thus, the cDNA that is to be mutated must be inserted into one of these vectors in order to generate single-stranded template. Production of the single-stranded template is described in sections 4.21–4.41 of Sambrook et al., supra.

In such techniques, to mutagenize the wild-type sialidase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type sialidase inserted in the vector, and the second strand of DNA encodes the mutated form inserted into the same vector. This heteroduplex molecule is then transformed into a suitable host cell, usually a prokaryote such as *E. coli* JM101. After growing the cells, they are plated on to agarose plates and screened using the oligonucleotide primer radiolabeled with 32-P to identify the colonies that contain the mutated form. These colonies are selected, and the DNA is sequenced to confirm the presence of mutations in the molecule.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitutions is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

C. Host Cell Cultures And Vectors

1. Prokaryotic Cells

Prokaryotes are the preferred host cells for initial cloning steps. They are particularly useful for rapid production of large amounts of DNA, for production of singlestranded DNA templates used for site-directed mutagenesis, for screening many mutants simultaneously, and for DNA sequencing of the mutants generated. Suitable prokaryotic host cells include *E. coli* K12 strain 294 (ATCC number 31,446), *E. coli* strain W3110 (ATCC number 27,325) *E. coli* X1776 (ATCC number 31,537), and *E. coli* B; however many other strains of *E. coli*, such as HB101, JM101, NM522, NM538, NM539, and many other species and genera of prokaryotes may be used as well.

Prokaryotes may also be used as hosts for expression of DNA sequences. The *E. coli* strains listed above, bacilli such as *Bacillus subtilis,* other enterobacteriaceae such as *Salmonella typhimurium* or *Serratia marcesans,* and various Pseudomonas species may all be used as hosts.

Plasmid vectors containing replicon and control sequences that are derived from species compatible with the host cell are used with these hosts. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUC118, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature,* 375:615 [1978]; Itakura et al., *Science,* 198:1056 [1977]; Goeddel et al., *Nature,* 281:544 [1979]) and a tryptophan (trp) promoter system (Goeddel et al., *Nucl. Acids Res.,* 8:4057 [1980];

EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell,* 20:269 [1980]).

2. Eukaryotic Microbes

Eukaryotic microbes such as yeasts may be used to practice this invention. The baker's yeast *Saccharomyces cerevisiae,* is a commonly used eukaryotic microorganism, although several other strains are available. The plasmid YRp7 (Stinchcomb et al., *Nature,* 282:39 [1979]; Kingsman et al., *Gene,* 7:141 [1979]; Tschemper et al., *Gene,* 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics,* 85:12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al.,*J. Biol. Chem.,* 255:2073 [1980]) or other glycolytic enzymes (Hess et al., *J. Adv. Enzyme Reg.,* 7:149 [1968]; Holland et al., *Biochemistry,* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

3. Eukaryotic Multicellular Organisms

Cell cultures derived from multicellular organisms may be used as hosts to practice this invention. While both invertebrate and vertebrate cell cultures are acceptable, vertebrate cell cultures, particularly mammalian cultures, are preferable. Examples of suitable cell lines include monkey kidney CVI line transformed by SV40 (COS-7, ATCC CRL 1651); human embryonic kidney line 293S (Graham et al., *J. Gen. Virol.,* 36:59 [1977]); baby hamster kidney cells (BHK, ATCC CCL 10); Chinese hamster ovary cells (Urlab and Chasin, *Proc. Natl. Acad. Sci USA,* 77:4216 [1980]); mouse sertoli cells (TM4, Mather, *Biol. Reprod.,* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.,* 85:1 [1980]); and TRI cells (Mather et al., *Annals N.Y. Acad. Sci.,* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus2, and most frequently Simian Virus 40 (5V40). The SV40 virus contains two promoters that are termed the early and late promoters. These promoters are particularly useful because they are both easily obtained from the virus as one DNA fragment that also contains the viral origin of replication (Tiers et al., *Nature,* 273:113 [1978]). Smaller or larger SV40 DNA fragments may also used, provided they contain the approximately 250-bp sequence extending from the HindIII site toward the Bg1-I site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, vsv, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells.

Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin (*Proc. Natl. Acad. Sci.* (USA), 77:4216 [1980]) are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC number CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Mammalian host cells may be cultured in a variety of media. Commercially available media such as Ham's F10 (Sigma), Minimal Essential Medium ([DMEM], Sigma), RPMI-1640 (Sigma), and Dulbecco's Modified Eagle's Medium ([DMEM], Sigma) are suitable for culturing the host cells. In addition, any of the media described in Ham and Wallace (*Meth. Enz.,* 58:44 [1979]), Barnes and Sato (*Anal. Biochem.,* 102:255 [1980]), U.S. Pat. Nos. 4,767,704; 4,657,866; 4,927,762; or 4,560,655; WO 90/03430; WO 87/00195; U.S. Pat. Re. 30,985; or copending U.S. Ser. No. 07/592,107 or 07/592,141, both filed on Oct. 3, 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin), trace elements (defined as inorganic compounds usually present at final concentrations in the micromolar range), and glucose or an equivalent energy source. Any other necessary supplements may also be included at appropriate concentrations that would be known to those skilled in the art.

4. Secretion Systems

Many eukaryotic proteins normally secreted from the cell contain an endogenous signal sequence as part of the amino acid sequence. This sequence targets the protein for export from the cell via the endoplasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, alanine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the 'pre-protein' or the immature form of the protein.

However, not all secreted proteins contain an amino terminal signal sequence that is cleaved. Some proteins, such as ovalbumin, contain a signal sequence that is located on an internal region of the protein. This sequence is not normally cleaved during translocation.

Proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA encoding the signal sequence portion of the gene is excised using appropriate restriction endonucleases and then ligated to the DNA encoding the protein to be secreted.

Selection of a functional signal sequence requires that the signal sequence is recognized by the host cell signal peptidase such that cleavage of that signal sequence and secretion of the protein will occur. The DNA and amino acid sequence encoding the signal sequence portion of several eukaryotic genes including, for example, human growth hormone, proinsulin, and proalbumin are known (see Stryer, *Biochemistry,* W. H. Freeman and Company, New York [1988], p. 769) and can be used as signal sequences in appropriate eukaryotic host cells. Yeast signal sequences, as for example acid phosphatase (Arima et al., *Nuc. Acids Res.,* 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 1988]), MalE, PhoA, or beta-lactamase, as well as other genes, may be used to target proteins from prokaryotic cells into the culture medium.

An alternative technique to provide a protein of interest with a signal sequence such that it may be secreted is to synthesize chemically the DNA encoding the signal sequence. In this method, both strands of an oligonucleotide encoding the selected signal sequence are chemically synthesized and then annealed to each other to form a duplex. The double-stranded oligonucleotide is then ligated to the 5' end of the DNA encoding the protein.

The construct containing the DNA encoding the protein with the signal sequence ligated to it can then be ligated into a suitable expression vector. This expression vector is transformed into an appropriate host cell and the protein of interest is expressed and secreted.

D. Transformation Methods

Cultures of mammalian host cells and other host cells that do not have rigid cell membrane barriers are usually transformed using the calcium phosphate method as originally described by Graham and Van der Eb (*Virology,* 52:546 [1978]) and modified as described in sections 16.32–16.37 of Sambrook et al. supra. However, other methods for introducing DNA into cells such as Polybrene (Kawai and Nishizawa, *Mol. Cell. Biol.,* 4:1172 [1984]), protoplast fusion (Schaffner, *Proc. Natl. Acad. Sci. USA,* 77:2163 [1980]), electroporation (Neumann et al., *EMBO J.,* 1:841 [1982]), and direct microinjection into nuclei (Capecchi, *Cell,* 22:479 [1980]) may also be used.

Yeast host cells are generally transformed using the polyethylene glycol method, as described by Hinnen (*Proc. Natl. Acad. Sci. U.S.A.,* 75:1929 [1978]).

Prokaryotic host cells or other host cells with rigid cell walls are preferably transformed using the calcium chloride method as described in section 1.82 of Sambrook et al., supra. Alternatively, electroporation may be used for transformation of these cells.

E. Cloning Methods

Construction of suitable vectors containing DNA encoding replication sequences, regulatory sequences, phenotypic selection genes and the foreign DNA of interest are prepared using standard recombinant DNA procedures. Isolated plasmids and DNA fragments are cleaved, tailored, and ligated together in a specific order to generate the desired vectors.

The DNA is cleaved using the appropriate restriction enzyme or enzymes in a suitable buffer. In general, about 0.2–1 µg of plasmid or DNA fragments is used with about 1–2 units of the appropriate restriction enzyme in about 20 µl of buffer solution. (Appropriate buffers, DNA concentrations, and incubation times and temperatures are specified by the manufacturers of the restriction enzymes.) Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases the ends will be directly compatible after endonuclease digestion. However, it may be necessary to first convert the sticky ends, commonly produced by endonuclease digestion, to blunt ends to make them compatible for ligation. To blunt the ends, the DNA is treated in a suitable buffer for at least 15 minutes at 15° C. with 10 units of the Klenow fragment of DNA Polymerase I (Klenow) in the presence of the four deoxynucleotide triphosphates. It is then purified by phenolchloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are present in solution in about equimolar amounts. The solution will also contain ATP, ligase buffer and a ligase such as T4 DNA ligase at about 10 units per 0.5 μg of DNA. If the DNA fragment is to be ligated into a vector, the vector is first linearized by cutting with the appropriate restriction endonuclease(s) and then phosphatased with either bacterial alkaline phosphatase or calf intestinal alkaline phosphatase. This prevents self-ligation of the vector during the ligation step.

After ligation, the vector with the foreign gene now inserted is transformed into a suitable host cell, most commonly a prokaryote such as $E$ $coli$ K12 strain 294 (ATCC number 31,446) or another suitable $E.$ $coli$ strain. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system described above. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res.*, 9:309 (1981) or by the method of Maxam et al., *Methods of Enzymology*, 65:499 (1980).

After mammalian host cells have been stably transformed with the DNA, the DHFR-protein-coding sequences are amplified by growing the host cell cultures in the presence of approximately 200–500 nM of methotrexate. The effective range of concentrations of MTX is highly dependent upon the nature of the DHFR gene and protein and the characteristics of the host. Clearly, generally defined upper and lower limits cannot be ascertained. Suitable concentrations of other folic acid analogs or other compounds that inhibit DHFR may also be used. MTX itself is, however, convenient, readily available, and effective.

A DNA sequence derived from sialidase encoding DNA but which cannot be functionally expressed may be used to "knock out" or otherwise disrupt the sialidase gene function of a cell line using a technique of homologous recombination. It is also possible to use this approach to disrupt sialidase gene function by targeting the promoter for the gene. A modification which disrupts gene function may be termed a "lesion" and may be an insertion, deletion, replacement or combination thereof, although it is perhaps simplest to use a DNA fragment which has a partial deletion of sialidase encoding sequence. A suitable deletion may be about 50 bp or more. A DNA construct containing the modified gene is introduced into the cell and recombination takes place between the construct and the genomic DNA of the cell.

A marker gene is incorporated in the construct to enable detection of a recombination event. The marker gene may be under the regulatory control of a promoter incorporated in the construct, which may be one inducible under suitable conditions. DNA analysis is needed, however, to determine whether recombination is at the correct genomic site. Such DNA analysis may be by probing for the insert and sequencing regions flanking the insert for the presence of sialidase sequence projecting beyond, or probing for the sialidase gene and detecting the modification which was made to the insert DNA.

Suitable techniques are described in International Patent Application WO91/01140 and in Hasty et al., Molecular and Cellular Biology, June 1992, 2464–2474, and are known to the person skilled in the art.

Where the target cells are diploid and have two copies of the sialidase gene, the two copies may be disrupted in turn, cells with one mutated copy being amplified and then used in a second stage involving inactivation or other disruption of the second copy of the gene. When no copy is functionally expressed, such cells may be detected by assaying for the absence of activity of the sialidase.

Another technique which may be used in the disruption of functional expression of a sialidase of a cell line, involves antisense RNA. DNA encoding sialidase may be introduced into the cells under the control of a promoter which ensures transcription of the strand of DNA other than the one used normally in the production of mRNA which is transcribed to produce the sialidase protein.

The antisense gene may be introduced into the cells in an expression vector which is maintained in the cells without integration into the genome. Suitable expression vectors are described above in the passage relating to cloning and expression in eukaryotic multicellular organisms. Alternatively, the gene may be incorporated into the genome of the cells by recombination. It is convenient to place the antisense gene under the control of a promoter which ensures transcription concurrently with transcription of the constitutive sialidase gene. The promoter may be inducible so that its activity can be precisely controlled.

The exact mode of action of antisense RNA in the disruption of normal gene function is not fully understood, although it at least partially involves hybridization of the antisense RNA to the complementary mRNA to form double-stranded RNA.

The following examples merely illustrate the best mode now contemplated for practicing the invention, but should not be construed as limiting its scope. All literature citations herein are expressly incorporated by reference.

Experimental Procedures

Procedures used in the Examples are now described.

Materials: 4-methylumbelliferyl-N-acetyl neuraminic acid, N-acetyl neuraminic acid, 2,3 sialyl lactose, 2,6-sialyl lactose, gangliosides, cholic acid, colominic acid and apotransferrin are from Sigma Chem. Co. (St. Louis, Mo). Sialic acid dimer and tetramer are from E.Y. Labs, Inc., (San Mateo, Calif.). The sialidase inhibitors; Neu5Ac2en, 9-azido-Neu5Ac2en, and 9-NANP-Neu5Ac2en are prepared as described earlier [Warner *Biochem. Biophys. Res. Commun.,* 148:1323 (1987) and Warner et al. *Carbohydr. Res.,* 215:315 (1991)].

Fluorescent sialidase assays: Standard assay conditions for monitoring the enzyme activity during purification using the fluorescent substrate analog are: 1.3 mM 4-MUNeu5Ac, 50 mM phosphate buffer, pH 6.8, 0.3 mg bovine serum albumin and varying amounts of enzyme in a total volume of 30 µl. After addition of enzyme the samples are incubated at 37° C. in a shaking water bath for 5 minutes. The reaction is terminated and the fluorescence of the liberated umbelliferone is enhanced by the addition of 2 ml of 80 mM glycine-carbonate buffer, pH 9.7. Quantification of the product is made by measuring the fluorescence of the samples with excitation at 365 nm and emission at 450 nm using a standard of 4-methyl umbelliferone. A unit of enzyme activity is defined as a µmol/min of sialic acid liberated.

Sialidase assays with natural substrates: When natural substrates are tested with the purified enzyme, the amount of released sialic acid is measured using the thiobarbituric acid assay as modified by Uchida [Uchida et al. *J. Biochem.,* 82:1425 (1977)] using sialic acid as standard. The amount of sialic acid in control samples, which include a complete assay mixture incubated without added enzyme is subtracted from each determination. all samples are cleared by centrifugation (1,000×G. 10 min) prior to determining the absorbance at 540 nm.

Protein assays: Protein determinations during purification are made using the commercial protein assay kit containing bicinchonic acid (BCA reagent) obtained from Pierce Chem. Co. (Rockford, Ill.). In the samples which contained glycerol, protein determinations are made with the Coomassie blue G-250 dye binding assay kit from BioRad Labs (Richmond, Calif.) which is based on the Bradford protein assay [Bradford, M. *Anal. Biochem.,* 72:248 (1976)]. Bovine serum albumin is a standard for both assays.

Enzyme kinetic parameters: Assay conditions (time and added enzyme) are modified for each substrate so that initial reaction rates are measured. Kinetic parameters are obtained from double reciprocal plots of the substrate saturation curves [Segel, I. H. John Wiley, New York, *Enzyme Kinetics,* 18 (1975)].

Acrylamide gel electrophoresis: Polyacrylamide gel electrophoresis is carried out as described by Laemmli (Laemmli, U. K. *Nature* 227:680 [1970]) using 12.5% acrylamide gels under denaturing conditions. Molecular weight markers are from Bio Rad.

Isoelectric Focusing Gel Electrophoresis: Isoelectric focusing analysis of the purified sialidase is carried out using plastic-backed, commercially prepared polyacrylamide gels (Pharmacia, Inc.) impregnated with ampholine buffers, pH 3–9. After electrophoresis, the gels are fixed, stained and destained as described by the manufacturer, except the Coomassie blue dye, G-250 is used for protein staining instead of Coomassie R-250. Marker proteins with known pI values are obtained from Serva (Heidelberg, Germany).

In some cases, the location of the sialidase is determined by enzyme assay of the gel. After electrophoresis, the gel is maintained at 4° C. on ice and overlaid with filter paper saturated in 50 mM phosphate buffer, pH 6.8, containing 1.3 mM 4-MU-Neu5Ac.

The gel is incubated in a shaking water bath at 37° C. for 10 min. After removal of the filter paper, the location of the enzyme is determined by inspection of the gel, monitoring for the fluorescent product with a hand-held ultraviolet light. (Mineralight model UVGL-25, UVP, Inc., San Gabriel, Calif.). The bands giving activity are marked by cutting the gel and then stained for protein. The isoelectric points of the protein samples analyzed are determined based on the anodal migration of each band, comparing to the migration of protein standards with know isoelectric points.

Isolation of sialidase tryptic peptides: A sample of the purified sialidase, 18 µg, in 180 µl of phosphate buffer is diluted by the addition of 20 µl of 0.1 M ammonium bicarbonate. TPCK-trypsin, 1.6 µg (Worthington, Inc., Freehold, N.J.) in 20 µl of 0.01 N HCl is added and the mixture incubated for 18 hr. at 37° C. The reaction is terminated by the addition of trifluoroacetic acid to 0.2% by volume and the solvent reduced to about 250 µl under vacuum.

The resulting peptides are isolated by reverse phase HPLC on a Vydac C-18 silica based column, 2.1×250 mm (The Separations Group, Inc., Hesperia, Calif.). The column is equilibrated in 0.1% trifluoroacetic acid and the peptides resolved from one another using a linear solvent gradient with increasing amounts of acetonitrile containing 0.1% trifluoroacetic acid, up to 100% in 76 min. at a flow rate of 0.25 ml/min at 30°, using an Hewlett-Package 1090 HPLC system. The effluent is monitored at 214 and 280 nm. About twenty fractions containing peptides are collected.

Amino terminal sequence analysis: Aliquots of several peptide fractions are subjected to N-terminal sequence analysis using an ABl 447A/120A sequencer. In general, the samples analyzed are in the 100–200 pmol range.

Protein Sequence Data Banks: The sequence of the tryptic peptides is examined for similarities to other known protein sequences. The data base as Genentech consists of protein sequences from the National Biomedical Research Foundations Protein Information resource, the SWISSPROT data base from EMBL, the Brookhaven Protein Data Bank and a number of protein sequences entered in-house.

Preparation of synthetic peptides and polyclonal antibodies: Polyclonal antisera are generated in female New Zealand White rabbits against synthetic peptides prepared based on several of the tryptic peptide sequences as described elsewhere (Bennett et al. *J. Biol. Chem.,* 266:23060 (1991)] The IgG fraction is isolated from the crude serum by column chromatography using commercially prepared 1.0 ml HiTrap Protein A columns, following the protocol supplied by the manufacturer (Pharmacia, Inc.). The resulting IgG fraction contains about 2 mg protein/ml.

Immunoblot Analysis: Cell extracts from several Chinese hamster ovary cells, grown in both serum-containing, and serum-free media, are prepared by suspending the cells, 10% w/v, in water, followed by sonic irradiation with three, five-second pulses using a Fisher Sonic Dismembrator model 300 (Fisher Scientific, Springfield, N.J.). The cell-free extracts are subjected to SDS-polyacrylamide gel analysis and electrophoretically transferred to polyvinylidene difluoride membrane [Matsudaria, P. *J. Biol. Chem.,* 262:10035 (1987)]. after the transfer is completed, the membrane is washed and incubated with the IgG fraction of the peptide antiserum diluted in blocking buffer as described by Burnette [Burnette, W. N. *Anal. Biochem.,* 112:195 (1981)]. Detection of the sialidase by immunoblot analysis is made using the isolated peptide antibody-IgG fraction, 1:1000 dilution, and a goat anti-rabbit IgG-horseradish peroxidase conjugate, 1:2000 dilution, (BioRad) with 4-chloro-napthol substrate.

Immunoblot Carbohydrate Analysis: Protein-bound carbohydrates are detected using a commercial glycan detection system (Boehringer) which is based on the oxidative immunoblot procedure described by Haselbeck and Hosel [Haselbeck et al. *Glycoconiugate J.,* 7:63 (1990)]. The staining protocol recommended by the manufacturer is followed except that the protein is transferred to a polyvinylidene difluoride membrane instead of nitrocellulose membrane and the blocking buffers contained 5% bovine serum albumin in 10 mM tris buffer, pH 7.4 with 0.9% sodium chloride. Detection is made with anti-digoxigenin antibodies linked with an alkaline phosphate conjugate (Boehringer), 1:1000 dilution in tris buffered saline using the phosphatase substrates, 4-nitroblue tetrazolium chloride, 0.03% (w/v) and 5-bromo-4Chloro-3- indoyl-phosphate 0.03% (w/v) in 100 mM tris buffer, pH 9.5, containing 100 mM sodium chloride and 50 mM magnesium chloride. The protein bands containing carbohydrate are usually visualized in about 10 to 15 min.

Digestion with peptide-N-glycosidase F: The purified sialidase (3 μg) or transferrin, as a control, is dialyzed extensively against 0.1 M ammonium bicarbonate and the solvent removed under vacuum. The residue is suspended in 14 μl of a buffer containing 0.18% SDS, 18 mM beta-mercaptoethanol, 90 mM phosphate, 3.6 mM EDTA, at pH 8.6, and heated at 100° C. for 3 min. After cooling to room temperature, the sample is divided into two equal parts. One aliquot is not treater further and serves as a control. The second fraction is adjusted to about 1% NP-40 detergent followed by 0.2 units of peptide-N-glycosidase F (Boehringer). Both samples are warmed at 37° C. for 2 hr. and then analyzed by SDS-polyacrylamide gel electrophoresis.

Cell Culture Conditions: Chinese hamster ovary cells, CHO 14.16 and CHO 12 are derived from the CHO-DUKX cell line (dhfr−) [Urlaub et al. *Proc. Natl. Acad. Sci.,* 77:4216 (1980)]. Lec 2 cells (ATCC number CRL 1736) are Chinese hamster ovary cells obtained from the American Type Culture Collection (Rockville, Md.). Cells are grown in either monolayer or suspension cultures in a high glucose-MEM media supplemented with fetal calf serum (10%). Monolayer cultures are grown to near confluence and are harvested by scraping the plate. Suspension cultures are harvested at a cell density of about $1.2-1.4 \times 10^6$ cells/ml. Cell viability is determined by trypan blue exclusion and only cultures with a viability of 90% or greater are employed for analysis.

EXAMPLE 1

Purification of Sialidase

The protocol for purification of the sialidase from about 100 l of cell culture fluid is summarized in TABLE I. The fluid is obtained from cultures of CHO 14.16 cells grown in a serum-free medium. After removal of the cell debris, the fluid is difiltered and concentrated about 10 fold using a 10 kDA polysulfone membrane (Millipore), reducing the isotonic salt concentration of the fluid to about 50 mM at pH 7.0. The concentrated cell culture fluid is directly subjected to DEAE-Sepharose chromatography. Under these chromatography conditions, the sialidase does not adhere to the column and appears in the effluent. The column flow-through is concentrated about 30 fold using a 10 kDa cellulose membrane filter (Millipore). The concentrated material is stored frozen at −20° C. and serves as the starting material for purification of the sialidase.

TABLE I

Purification of CHO Cell Sialidase
Enzyme isolated from about 100 l of cell culture fluid.[a]

| | Step | Total Protein (mg) | Specific Activity[b] (μmol/min-mg) | Purification (fold) | Yield (%) |
|---|---|---|---|---|---|
| 1. | DEAE-Sepharose flow-through | 22,500 | $1.45 \times 10^{-3}$ | 1 | 100 |
| 2. | Ammonium Sulfate | 8,250 | $2.65 \times 10^{-3}$ | 2 | 67 |
| 3. | DEAE-Sepharose | 1,450 | $7.88 \times 10^{-3}$ | 5 | 35 |
| 4. | S-Sepharose | 55 | 0.149 | 103 | 25 |
| 5. | Hydrophobic interaction chromatography | 31 | 0.214 | 148 | 20 |
| 6. | Heparin-Agarose | 3.6 | 1.27 | 876 | 13 |
| 7. | Chromatofocusing | 0.174 | 10.1 | 6,963 | 6 |

[a]Specific activity of the sialidase in the crude cell culture fluid estimated to be about $0.3 \times 10^{-3}$ nmol/min/mg protein.
[b]4-MU-Neu5Ac employed as substrate. Assays carried out at pH 6.8 to minimize the contribution by the lysosomal sialidase which may be present in the initial stages of the purification.

The purification of the enzyme is monitored at each step using 4-MU-Neu5Ac as substrate. The final purified material is tested with several naturally occurring sialyl conjugate substrates. all purification steps are carried at out 4° C.

Step 1: Ammonium sulfate precipitation: About 1 l of DEAE-Sepharose concentrate (equivalent to about 100 l of cell culture fluid) is cleared by centrifugation at 13,000×g at 4° C. for 20 min. after removal of the pellet, the supernatant is adjusted to 47% saturation by the addition of solid ammonium sulfate. after centrifugation (17,000×g, 20 min., 4° C.) the supernatant is discarded and the pellet resuspended by repetitive aspiration with a pipette using 30 ml. of 2.5 mM phosphate, pH 6.8, 1 mM EDTA (Buffer A). (Unless noted, all buffers used during purification contain 1 mM EDTA). The solution is dialyzed overnight against 3 changes of 4 l of Buffer A.

Step 2: DEAE Chromatography: After dialysis the enzyme preparation is applied to a column (5×15 cm) containing DEAE-Sepharose FF (Pharmacia) equilibrated in Buffer A. The column is eluted with 225 ml Buffer A: this eluate is discarded. Further elution is carried out with 250 ml 10 mM phosphate, pH 6.8, 1 mM EDTA, (4×Buffer A) followed by 600 ml 20 mM phosphate, Ph 6.8, 1 mM EDTA, collecting 8 ml fractions. Fractions containing the enzyme activity are pooled and the pH adjusted to pH 6.0 with dilute HCl.

Step 3: S-Sepharose chromatography: The enzyme preparation from the previous step is applied with a peristaltic pump to a column (2.5×7.5 cm) containing S-Sepharose fast flow (Pharmacia) in 4×Buffer A at pH 6.0. The column is washed with about 25 ml of 10 mM phosphate buffer, pH 6.0. Further elution is carried out with a linear gradient of a buffer with increasing phosphate concentration, from 10 to 150 mM in a total of 400 ml, collecting 5 ml fractions. The column flow rate is maintained with a peristaltic pump at about 2 ml/min. The activity eluted over a broad range of the gradient. With some preparations, the major peak of activity is partially resolved into two fractions with nearly equal sialidase levels. Examination of these fractions with polyacrylamide isoelectric focusing indicates that they each contain several isoelectric enzyme forms. Since neither fraction contains a single enzyme form, both fractions are combined and purified together as a mixture.

Step 4: Hydrophobic interaction chromatography: The S-Sepharose material is brought to 2M ammonium sulfate, adjusted to pH 6.0, and then applied to a Phenyl-Toyopearl 650S column, 1.5×7 cm, equilibrated in a buffer containing 50 mM phosphate, pH 6.0, 1 mM EDTA and 2 M ammonium sulfate. After loading, the column is washed with 20 ml. of equilibration buffer and then eluted with a linear gradient of decreasing ammonium sulfate in the buffer, about 55 gms of each buffer or about 100 ml of total gradient are used. Two ml fractions are collected. after the fractions containing enzyme activity are located, they are pooled and then dialyzed overnight against 1 l of 5 mM phosphate, pH 6.8, 1 mM EDTA with 10% glycerol.

Step 5: Heparin-Agarose chromatography: The dialyzed sample from the previous step is applied directly to a column containing heparin-agarose (sigma) 1.0×7 cm equilibrated in 5 mM phosphate, pH 6.8, 1 mM EDTA containing 50 mM NaCl. After loading with the aid of a peristaltic pump, the column is washed with 8 ml of the equilibration buffer and the enzyme then eluted with a linear gradient 120 ml total of equilibration buffer and increasing concentration of sodium chloride up to 500 mM. Fractions of 1.5 ml were collected. The fractions containing activity are pooled and concentrated further by adjusting to 2 M ammonium sulfate and applying to a small column of Phenyl-Toyopearl, 0.5×1.0 cm and eluting with 2 ml 5 mM phosphate, 1 mM EDTA. The concentrated enzyme solution is dialyzed against 1 l of the eluting buffer with 10% glycerol.

Step 6: Chromatofocusing Chromatography: The concentrated enzyme preparation from the previous step is diluted with an equal volume of tris-HCl, 25 mM, pH 8.0 and 25 mM sodium chloride. The mixture is adjusted to pH 8.0 with dilute hydroxide and then applied to a DEAE-Sepharose column 1.0×18 cm equilibrated in the tris buffer. after loading, the column is washed with 8 ml of the equilibration buffer. The enzyme is eluted with Polybuffer 96 (Pharmacia) diluted 1:12 and adjusted to pH 6.0 with HCl. Two ml fractions are collected, with a flow rate of about 0.5 ml/min provided by a peristaltic pump. The enzyme elutes as a sharp peak at pH 7.0–7.4, in a total volume of about 9.0 ml, FIG. 1. The pooled fractions are immediately adjusted to 2 M ammonium sulfate and pH 6.0 with HCl and then concentrated by applying to a small Phenyl-Toyopearl column, 1.0×1.0 cm, equilibrated in 5 mM phosphate, pH 6.8, 1 mM EDTA, with 10% glycerol and 2M ammonium sulfate. After application of the sample, the column is washed with 5 ml of the equilibration buffer to remove the Polybuffer. The enzyme is eluted by washing the column with 1.5 ml of 5 mM phosphate, pH 6.8, 1 mM EDTA with 20% glycerol and dialyzed overnight against 1 l of the eluting buffer.

EXAMPLE 2

Evaluation of Enzyme Purity and Characterization of the Enzyme

Figure 2:
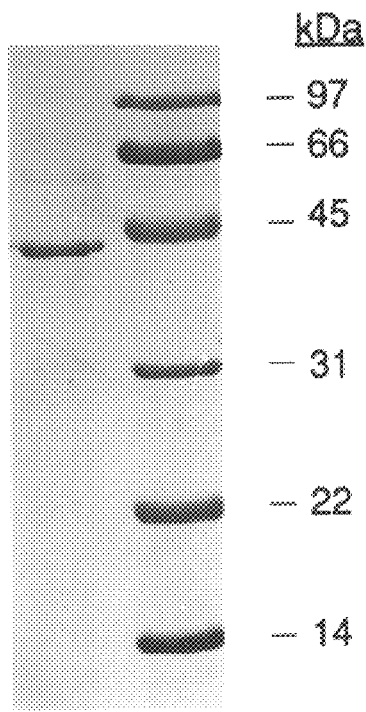
FIG. 2: SDS polyacrylamide gel of the purified CHO cell sialidase stained for protein. Lane A: CHO cell sialidase, 2 μg. Lane B: molecular weight standards, phosphorylase b, 97,400; bovine serum albumin, 66,200; ovalbumin, 45,000; carbonic anhydrase, 31,000; soybean trypsin inhibitor, 21,500; and lysozyme, 14,400.

Analysis with SDS Polyacrylamide Gel Electrophoresis: The final purified sialidase preparation gives a single major protein band at a molecular weight of 43 kDA when analyzed by SDS-polyacrylamide gel electrophoresis under reducing conditions, FIG. 2. A minor contaminant is detected at about 60 kDa and estimated to be less than 1% of the total material analyzed. A similar result is obtained when the sample is analyzed in the absence of a reducing reagent except that the protein band at 43 kDA is considerably more diffuse.

Figure 3:
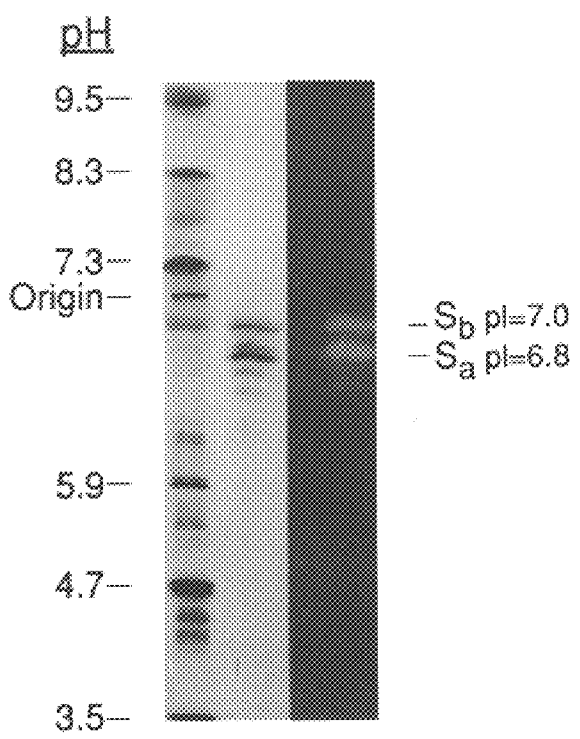
FIG. 3: Polyacrylamide isoelectric focusing gel of the purified CHO cell sialidase. The gel was developed as described in Methods and stained for protein. Lane 1: Protein standards; ribonuclease, pI=9.5; myoglobin whale (recombinant), pI=8.3; myoglobin horse, pI=7.3; conalbumin, pI=5.9; bovine serum albumin, pI=4.7; amyloglucosidase, pI=3.5. Lane b: Purified CHO sialidase, $S_a$ and $S_b$, 2 μg total load. Lane C: Gel stained with fluorogenic substrate. Prior to protein staining, the gel was impregnated with 4-MU-Neu5Ac and incubated at 37° C. The gel was visualized under ultraviolet light in order to detect those bands with sialidase activity.
Figure 4:
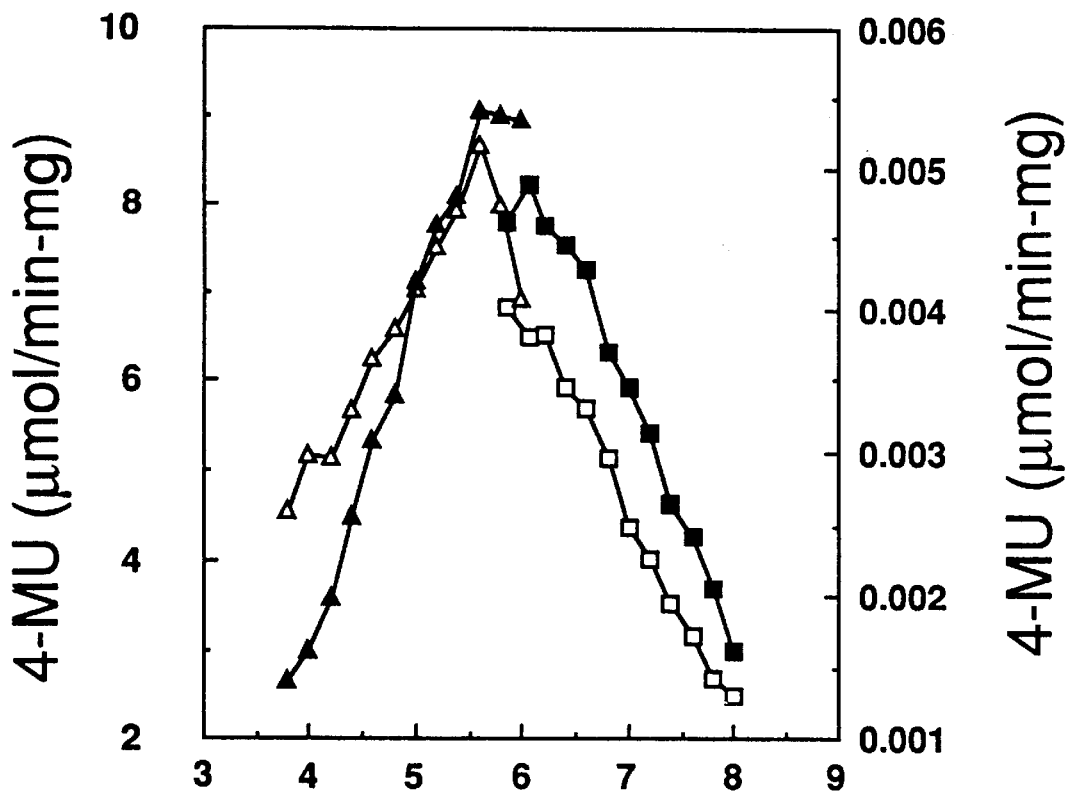
FIG. 4: Enzyme activity dependence on pH. Assays were carried out with either the purified enzyme) solid filled points or crude cell lysates (clear points) using 4-MU-Neu5Ac as substrate (see Methods). Phosphate buffer: squares. Acetate buffer: triangles.

Isoelectric Focusing Analysis: When the purified sialidase preparation is subjected to polyacrylamide gel isoelectric focusing, at least two major protein bands are detected along with about five minor bands, FIG. 3, panel B. The two major protein bands, $S_a$ and $S_b$, give isoelectric points of pI=6.8 and 7.0, respectively. Interestingly, all of the protein bands have sialidase activity when the gel is visualized with impregnated fluorogenic substrate, FIG. 3, panel C. The level of activity in each band is proportional to the intensity of the protein staining.

pH Optimum and Stability: The purified enzyme exhibits considerable activity over a broad pH range, extending from pH 4.5 to 7.5, with the optimum at about pH 5.9, FIG. 4. A similar result is obtained when the enzyme is assayed in crude cell homogenates, except that the level of activity in the acidic range, pH 3.5–4.5 is slightly greater than with the purified enzyme, FIG. 4. We assume that this activity is due to the presence of the lysosomal sialidase in the crude homogenate which has a pH optimum in the acidic region [Warner et al. *Biochemistry*, 18:2783 (1979)].

The protein is stable during purification and the fractions are stored frozen at −20° C. between purification steps when necessary. However, after chromatofocusing, the final enzyme preparation is very thermal labile and requires the presence of 20% glycerol to maintain the activity during dialysis. Even when 20% glycerol is included, about 15% of the activity is lost upon a single freeze thaw cycle. The final material is stable for three months when stored frozen at −70° C.

As a result of the thermal lability of the purified enzyme, bovine serum albumin (0.3 mg/ml) is included in the assay to insure that linear assay conditions are maintained when the kinetic parameters of the various substrates are evaluated.

Substrate specificity: Several classes of sialyl glycoconjugates are tested as substrates, TABLE II. Oligosaccharides such as sialyl lactose are readily cleaved; although the enzyme shows about a 4-fold preference for 2,3-linked sialic acid residues. This is not surprising since rodent-derived glycoproteins contain, nearly exclusively, sialic acid in 2,3-linkages. The oligosaccharide side chains on intact glycoproteins are also substrates. Sialic acid bound to human serum transferrin is cleaved much more slowly than that bound to recombinant human deoxyribonuclease 1. The difference in $V_{max}$ values between these two protein substrates is probably also due to the sialic acid linkage differences. Transferrin is isolated from human serum and contains only 2,6 linked sialic acid residues [Baenziger, J. U. *The Plasma Proteins 2nd Ed.* (Putnam, F. W., ed.) 272–398, Academic Press, New York (1984)]. In contrast, deoxyribonuclease 1, although it is coded by a human genetic construct, it is expressed in Chinese hamster ovary cells and therefore presumably contains only 2,3-linked sialic acids. The $K_m$ values for both proteins are nearly identical. Sialic acid dimers (isolated from colominic acid hydrolysates) in 2,8-linkages are also substrates for the enzyme. Higher oligomeric sialic acids such as sialic acid tetrameres and colominic acid are also hydrolyzed but at substantially reduced rates.

TABLE II

Sialidase Kinetic Constants With Soluble Sialylgylcoconjugate Substrates[a]

| Substrate | $V_{max}$ ($\mu$mol/min-mg) | $K_m$ (mM) |
|---|---|---|
| 4-MU-Neu5Ac | 18 | 0.4 |
| α-2,3 Sialyllactose | 16 | 1.3 |
| α-2,6 Sialyllactose | 4 | 1.2 |
| Transferrin | 2 | 4.1 |

TABLE II-continued

Sialidase Kinetic Constants With Soluble Sialylgylcoconjugate Substrates[a]

| Substrate | $V_{max}$ (μmol/min-mg) | $K_m$ (mM) |
| --- | --- | --- |
| rDeoxyribonuclease 1 | 12 | 5.8 |
| Sialic acid dimer | 11 | 3.4 |
| Sialic acid tetramer | 3 | 2.4 |

[a]Standard assay conditions employed for all substrates. Apparent $K_m$ and $V_{max}$ values determined as described in Methods. Shown are the averages of duplicate determinations with a relative error of about 10% between each determination.

Some gangliosides are degraded by the sialidase, TABLE III; although these substrates require the presence of cholic acid as a solubilizing agent in the assay for optimal activity. The gangliosides, $G_{M3}$, $G_{D1a}$, and $G_{T1b}$ are hydrolyzed at comparable rates while $G_{M1}$, $G_{M2}$, and $G_{D1b}$ are not substrates. These results are consistent with the enzyme displaying a preference for sialic acid residues linked at the terminus of the oligosaccharide chain. Internally bound sialic acid residues like those on $G_{M1}$ and other gangliosides are apparently not accessible to the enzyme.

TABLE III

Sialidase Activity Toward Gangliosides and Colominic Acid[a]

| Substrate | Relative Activity (%) |
| --- | --- |
| α-2,3 Sialyllactose | 100 |
| Gangliosides/Cholic Acid | |
| $G_{M1}$ | NR[b] |
| $G_{M2}$ | NR[b] |
| $G_{M3}$ | 29 |
| $G_{D1a}$ | 21 |
| $G_{D1b}$ | NR[b] |
| $G_{T1b}$ | 23 |
| Colominic Acid | 4 |

[a]All substrates tested at 4 mM and assayed under initial rate conditions at pH 6.0. Cholic acid (0.05%) included with the lipid substrates. Optimal conditions determined with $G_{M3}$ as substrate using the thiobarbiturate assay for sialic acid.
[b]NR = no reaction products detected.

Figure 5:
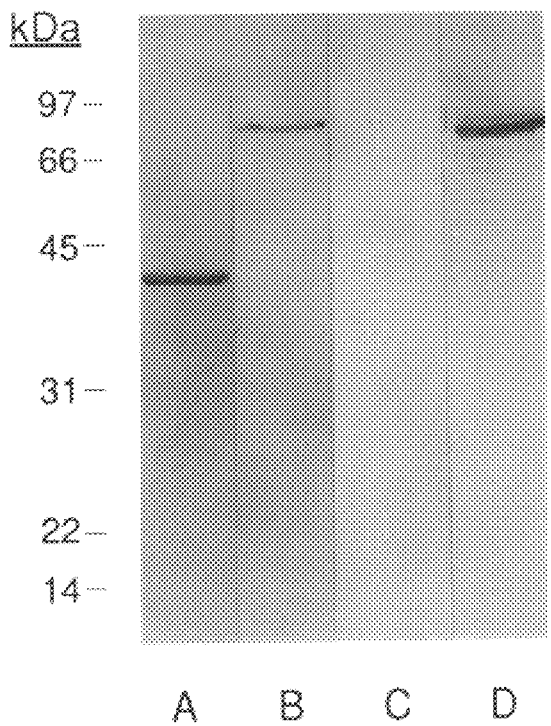
FIG. 5: Immunoblot detection of carbohydrate on CHO cell sialidase on polyvinylidine difluoride membrane. Sialidase (1.5 μg) and transferrin (0.8 μg) were subjected to SDS polyacrylamide gel electrophoresis and electrophoretically transferred to the membrane. Lanes A and B: sialidase and transferrin, respectively, staining for protein. Lanes C and D: sialidase and transferrin, respectively staining for carbohydrate. The membrane was treated with sodium metaperiodate and carbohydrates were reacted with digoxigenin-3-O-succinyl-εaminocaproic acid hydrazide. After treatment with anti-digoxigenin-antibody conjugated with alkaline phosphatase the glycoproteins were detected by incubating with alkaline phosphatase substrates.

Carbohydrate detection: The presence of multiple electrophoretic forms, FIG. 3, might suggest that the sialidase may be a glycoprotein containing a heterogeneous mixture of oligosaccharide side chains with differing charged groups. For this reason, the protein is analyzed for carbohydrates using the oxidative-immunoblot method described by Haselbeck and Hosel (supra.), FIG. 5. With this assay, no carbohydrates are detected on the sialidase (1.5 μg), FIG. 5, lane C. In contrast, a strong signal is observed from the oligosaccharide side chains of transferrin (0.8 μg) even though a smaller amount of this glucoprotein is tested, FIG. 5, lane D. In experiments not shown, we estimate the limits of detection with the immunoblot assay to be about 80 ng of blotted glycoprotein.

In other experiments (data not shown), the sialidase is digested with peptide-N-glycosidase F, an endoglycohydrolase that cleaves nearly all types of asparagine linked carbohydrate side chains from denatured proteins [Tarentino, A. L., et al., Biochemistry, 24:4665 (1985)]. This treatment is without effect on the enzyme when analyzed with SDS-polyacrylamide gel electrophoresis also indicating that the sialidase does not contain carbohydrates side chains.

The observed multiple electrophoretic forms of the purified enzyme must arise due to charge heterogeneity introduced into the protein by other means, possibly proteolytic clipping of the polypeptide or deaminidation of asparagine residues [Wright, H. T., Crit. Rev. Biochem. and Mol. Biol., 26:1 (1952)].

Figure 6:
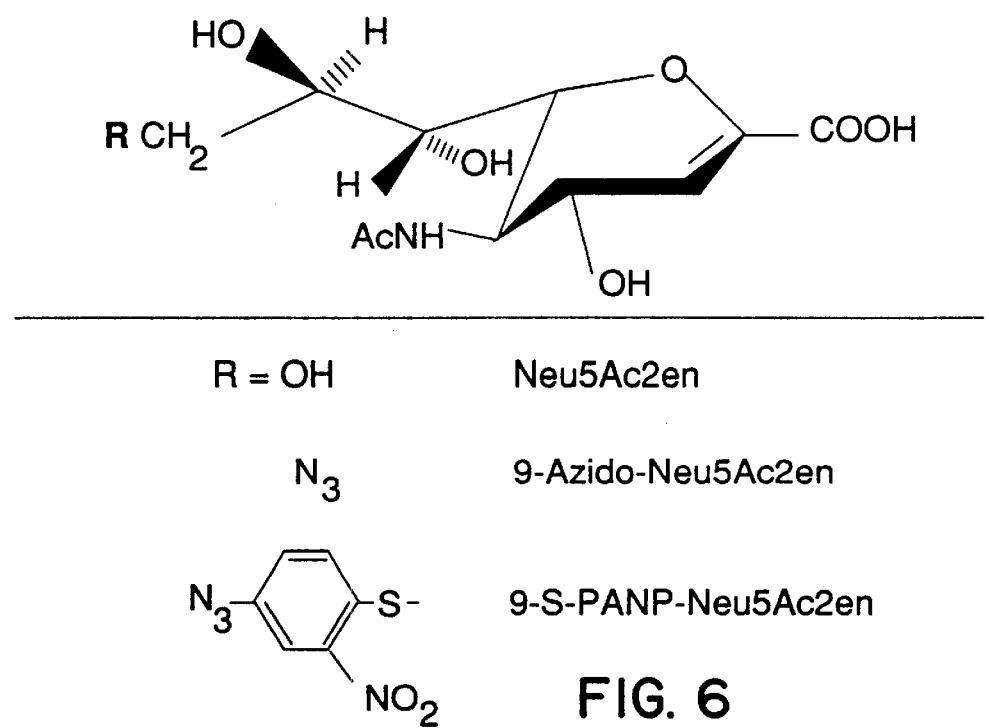
FIG. 6: Neu5Ac2en derivatives tested as sialidase inhibitors. Compounds were synthesized as described in Methods.

Inhibitor Studies: The potency of several sialidase competitive inhibitors is evaluated with the purified enzyme and their Ki values compared with sialidases from other sources, FIG. 6, TABLE IV. The well known microbial sialidase inhibitor, Neu5Ac2en, a potent inhibitor of the CHO cell enzyme, giving a Ki of about 10 μM. Derivatives of Neu5Ac2en which contain substituents in place of the C-9 hydroxyl group are also evaluated as enzyme inhibitors. Modifications include substitution with azide and nitrophenyl azide groups, give rise to 9-azido-Neu5Ac2en and 9-PANP-Neu5Ac2en, respectively, FIG. 6. In contrast to the lysosomal and plasma membrane sialidase, which are strongly inhibited by both modified Neu5Ac2en molecules, the CHO cell-sialidase is moderately inhibited by 9-azido-Neu5Ac2en, Ki=45 μM, and weakly inhibited by 9-PANP-Neu5Ac2en, Ki=300 μM. Previous analysis of the cytosolic sialidase from rat muscle gave results similar to that obtained with the CHO enzyme (Warner, T. G., Louie, A., Potier, M. and Ribeiro, A., (1991) Carbohydr. Res. 215:315).

TABLE IV

Inhibition Constants For CHO Cell Sialidase And Neu5Ac2en Derivatives[a]

| | | $K_i$ (μM) | | |
| --- | --- | --- | --- | --- |
| Sialidase Source | Cellular Localization | Neu5Ac2en | 9-Azido Neu5Ac2en | 9-S-PANP Neu5Ac2en |
| Chinese Hamster Ovary Cells | Cytosol ? | 10 | 45 | 300 |
| Rat muscle[b] | Cytosol | 10 | 50 | NI[c] |
| Fibroblasts[b] | Lysosome | 10 | 10 | 10 |
| Adenovirus[b] | Plasma Membrane | 10 | 10 | 10 |
| Transformed Kidney Cells | | | | |

[a]Sialidase assayed with 4-MU-Neu5Ac as substrate and inhibitory constants determined as described in Methods.
[b]Taken from previously reported data (see Warner, T. G., Biochem. Biophys. Res. Commun., 148:1323 (1987); Warner, T. G., et al., Carbohydr. Res., 215:315 (1991)).
[c]NI = not inhibited. Previous kinetic experiments not carried out at a high enough inhibitor concentration to determine Ki values above 50 μM.

EXAMPLE 3

Antibody Detection of Sialidase in CHO Cell Homogenates

The sialidase described is purified exclusively from the cell culture fluid of a single production cell line (CHO 14.16), so lysates of this, as well as other, unrelated CHO cells are examined for the enzyme in order to gain insight into its frequency of expression in the CHO cell lineage. Direct enzyme assays of the cell homogenates for the sialidase might be complicated by the presence of the lysosomal sialidase and perhaps other cellular sialidases which may have activity extending into the neutral pH range.

The purified protein is digested with trypsin and tryptic peptides so obtained are sequenced. FIG. 8 shows the sequences of 11 tryptic peptides of the of sialidase (SEQ ID NOS: 1–11). On comparison of the amino acid sequence of tryptic fragments (SEQ ID NOS: 1–11) with the sequences of microbial sialidases and other mammalian proteins using sequence data bases, no significant sequence similarities are found for SEQ ID. No. 11.

Figure 7:
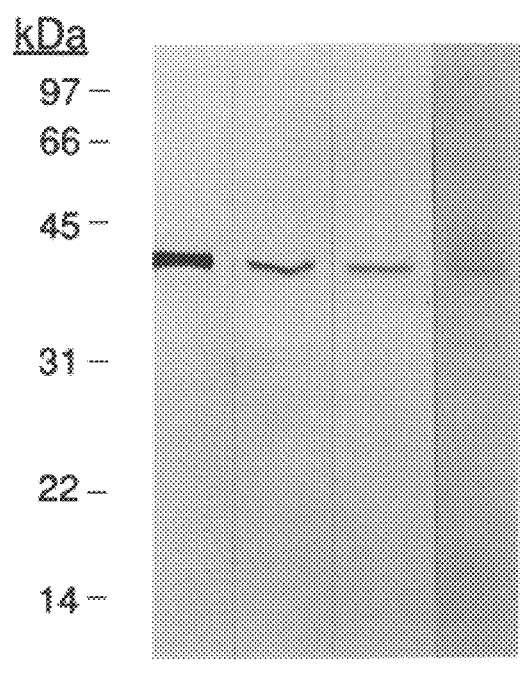
FIG. 7: Irnmunoblot detection of sialidase in crude cell extracts. Homogenates of various CHO cell lines were subjected to SDS polyacrylamide gel electrophoresis and transferred to nitrocellulose membrane as described in Methods. The sialidase in each preparation was visualized using peptide antibody, overlaying with goat-anti rabbit igG-horseradish peroxidase conjugate. Lane A: purified sialidase 0.03 μg, Lane B: CHO 14.16 (200 μg protein), Lane C: CHO 12 (200 μg protein), Lane D: Lec 2 (200 μg protein).

Highly specific antibodies to a synthetic peptide based on the amino acid sequence, SEQ. ID NO. 11, CRVQAQSPNSGLDFQDN, obtained from trypsin digestion of the purified protein are prepared and used in monitoring for the presence of the sialidase using immunoblots of the cell extracts, FIG. 7. The purified enzyme gives a strong signal at about 43 kDa with the peptide antibody. A similar result is also obtained with cell extracts of the CHO 14.16 cell line and extracts from several unrelated CHO cell lines. These results demonstrate that the enzyme is not limited to the specific cell line employed for its purification. However, the sialidase levels vary slightly between different cell lines.

EXAMPLE 4

Synthesis of Oligonucleotide Probes

The uniqueness of Seq. ID. No. 11 makes it useful for the construction of an oligonucleotide probe for the sialidase gene to be used in the "long probe" technique, as described in Ullrich, A., Berman, C. H., Dull, T. J., Gray, A., and Lee, J. M., The EMBO Journal 3, no. 2, 361–364, (1984), also U.S. Ser. No. 07/841,868 (European Patent application no. 84303784.7). This technique requires the synthesis of a single probe which has a nucleotide sequence which is one of the many possible sequences which encode the amino acid sequences. See Example 4.

An oligonucleotide is synthesized using the method of Crea, R., and Horn, T., Nucleic Acids Research, 8, 2231 (1908). The oligonucleotide is synthesized on a solid cellulose support by sequential addition of fully protected monomer-, dimer-, or trimer-blocks. The final 51 nucleotide polymer is treated with base (aq. conc. NH3) and acid (80% aq. HOAc), the polymer pelleted off and the supernatant evaporated to dryness. The residue, dissolved in 4% aq. NH3 is washed with ether (3×) and used for the isolation of the fully deprotected fragment. Purification is accomplished on a 15% polyacrylamide gel and recovery by electroelution and ethanol precipitation.

EXAMPLE 5

Obtention of Sialidase-encoding DNA Preparation of Genomic Library

DNA from Chinese hamster ovary cells is prepared according to the procedure of Blin and Stafford, *Nucleic Acid Research*, 3:2303 (1976) and subjected to a non-limited digestion with the restriction endonucleases HaeIII and AluI. The products are size-fractionated by sucrose gradient centrifugation. See Maniatis et al., *Cell*, 15:1157 (1978). Large fragments (15–20 kb) are isolated and treated with EcoRI methylase to render EcoRI sites within the DNA resistant to cleavage with EcoRI. Synthetic dodecameric DNA molecules bearing an EcoRI cleavage site (EcoRI linkers) are ligated to the methylated DNA and digested with EcoRI to generate EcoRI cohesive ends. Following an additional size selection (15–20 kb), the DNA is suitable for insertion into the bacteriophage cloning vector, Charon 4A (λCH4A).

Foreign DNA can be inserted into the λCH4A vector after the removal of two internal EcoRI fragments which contain genes non-essential for phage growth. The two "arms" of the bacteriophage DNA are annealed through their 12 base pair cohesive ends and joined to the DNA by ligation of the EcoRI cohesive ends. The ligation reaction is performed at a high DNA concentration to promote the formation of long concatemeric DNA molecules which are the substrates for in vitro packaging. Approximately $1 \times 10^6$ in vitro packaged phage are amplified $10^6$ fold by low density growth on agar plates to establish a permanent library of cloned DNA fragments.

Screening the Genomic Library

The HaeIII-Alu library is screened using the in situ plaque hybridization technique of Bentn and Davis, *Science*, 196:180 (1977). 100,000 recombinant phage are plated on $3.1 \times 10^8$ exponential phase bacterial cells on 15 cm NZCYM petri dishes. To prevent top agar from adhering to the nitrocellulose filter when it is lifted from the plate (which tends to increase the background hybridization), plates are dried in a 37° C. incubator for several hours or set on edge overnight to drain excess liquid. The use of 0.7 percent agarose rather than agar in the top agar layer also minimizes this problem. The plates are incubated at 37° C. for 14–16 hrs., at which time the plaques are confluent. Plates are refrigerated for an hour or longer before the filters are applied. Nitrocellulose filters (pore size 0.45 μm) fit easily over the agar plate. Phage and DNA are adsorbed to these filters in duplicate, 1a and 1b, 2a and 2b, etc., by placing two filters on each plate sequentially, 5 min. for each, at room temperature. Small holes are made with a needle filled with ink to orient the filters on the plates. The DNA is denatured and bound to the filters as described by Benton and Davis, supra.

To prepare the filters for hybridization to a labeled synthetic probe, they are wetted in about 10 ml per filter of 5× SET, 5× Denhardt's solution (5× Denhardt's solution=0.1 percent bovine serum albumin, 0.1 percent polyvinylpyrrolidone, 0.1 percent Ficoll; Denhardt, *Biochem. Biophys. Res. Comun.*, 23:641 (1966), 50 g/ml denatured salmon spem DNA, 0.1 percent sodium pyrophosphate and 2 percent formamide. The filters are prehybridized with continuous agitation at 42° C. for 14–16 hrs. The filters are hybridized with agitation at 42° C. in prehybridization solution containing a $^{32}$P-labeled hybridization probe. The synthetic probe for sialidase is labeled using the procedure of Taylor et al., *Biochem. Biophys. Acta*, 442:324 (1976). After hybridization, the filters are washed 6× with agitation in about 15 ml per filter of 0.1 percent SDS, 0.1 percent sodium pyrophosphate, 0.2× SET at 37° C. for 45 min. The filters are blotted dry, mounted on cardboard and exposed to Kodak XR5 X-ray film with Dupont Cronex 11R Xtra Life Lightning-plus intensifying screens at −70° C. for 1–2 days.

Plaque Purification of Recombinant Phage

Plaques from the region of a plate corresponding to a positive on the autoradiogram are picked and suspended in 0.5 ml PSB. The phage suspension is titered and the plate containing about 1,000 plaques is rescreened. The process of picking positives and rescreening is repeated until 90 percent of the plaques on a plate give positive signals after screening. Single phage are suspended in 1.0 ml PSB (0.05 percent gelatin, 0.10 M NaCl, 0.01 M Tris pH 7.4, 0.01 M $MgCl_2$) at 37° C. for 2 hrs. 50 is added to 0.2 ml of exponential phase bacterial cells+0.2 ml of 10 mM $MgCl_2$, 10 mM $CaCl_2$, 37/15". This is added to 50 mls NZYDT medium at 37° C. for 14–16 hrs. Chloroform +3 g NaCl is added and the bacteria removed by pelleting 15"/5 K. 3.5 g of polyethylene glycol is added to the supernatant/1 hr. 0. The phage precipitate and are pelleted by spinning 20"/5 K.

The pellet is resuspended in 2.0 mls PSB+1.0 g CsCl and layered on 0.9 ml steps of 1.7, 1.5 and 1.45 g/cc CsCl in PSB. The gradient is spun at 25 K in a Sorval 50 Ti for 3 hrs. The phage band is collected and dialyzed 14–16 hrs. against 0.1M NaCl, 50 mM Tris-Cl (pJ 7.5) and 10 mM $MgSO_4$. The phage DNA is extracted with phenol equilibrated with 10 mM Tris, 1 mM EDTA. The phenol is removed with chloroform and the DNA precipitated with 100 percent ethanol. The DNA is resuspended in water and restricted with EcoRI at 37° C. The digested DNA is run on a 1 percent agarose gel. Blot hybridization analysis of DNA digests is carried out according to Southern, *J. Mol. Biol.*, 98:503 (1975). These filters are probed under the same conditions as the phage library with the synthetic sialidase probe. The fragment that hybridize is cloned into M13 (ATCC 15669-B1). Plaque lifts are done as previously described and DNA made from the hybridizing plaques.

The DNA encodes the sialidase and when expressed produces the sialidase protein, determined using a florescent sialidase assay described supra.

The sialidase gene is sequenced using the technique of Maxam and Gilbert, described in Methods in Enzymology (1980) 65 (part 1), 497–559.

Transcription of the genomic sialidase-encoding DNA produces mRNA for use in synthesis of cDNA lacking any introns. cDNA is synthesized as described in Maniatis et al., Molecular Cloning—A Laboratory Manual, 1982, Cold Spring Harbor Laboratory.

EXAMPLE 6

Production of Recombinant Cells Wherein a Constitutive Sialidase Gene is not Functionally Expressed, by Homologous Recombination The technique used here is described fully in WO 91/01140.

A vector to be used in inactivation of functional sialidase expression is constructed from a restriction fragment of the genomic DNA encoding sialidase obtained in Example 5. The restriction fragment lacks a part of the sialidase gene so that its expression does not lead to production of a functional sialidase. The restriction fragment is cloned into plasmid pBR322 and a selectable marker gene introduced into the fragment.

DNA comprising the defective sialidase gene and selectable marker gene is introduced into Chinese hamster ovary cells by microinjection (Capecchi, Cell 22, 479–488 (1980)) and the cells are grown in medium selective for the marker. Growth in the medium establishes that the defective sialidase gene has integrated into the genome of the cells. Cells from colonies which grow are isolated and analyzed to identify those in which the integration of the defective sialidase gene has taken place by homologous recombination with the wild-type gene as opposed to integration by non-homologous recombination at another site in the genome. This is done by using oligonucleotide probes for the insert, a Southern blot assay and then sequencing the 5' and 3' regions of the DNA obtained for the presence of sialidase-encoding sequence extending beyond the inserted DNA.

Cells demonstrating inactivation of one copy of the sialidase gene are used for inactivation of the second copy.

The introduction of defective sialidase gene with a selectable marker is repeated. Cells in which both copies of the sialidase gene have been inactivated are identified by the absence of functional expression of sialidase activity, determined using the fluorescent sialidase assay described supra.

EXAMPLE 7

Production of Recombinant Cells Wherein a Constitutive Sialidase Gene is not Functionally Expressed, Using Antisense RNA DNA encoding the sialidase is inserted into a mammalian expression vector under the control of a promoter which ensures transcription of the strand of DNA which is not the one transcribed into mRNA. The vector is introduced into Chinese hamster ovary cells under conditions in which transcription occur.

Sialidase activity is assayed using the fluorescence techniques used in the preceding examples. No or very little sialidase activity is found, as a result of interaction of antisense RNA with the sialidase mRNA. Constitutive sialidase activity is disrupted so that there is no functional expression.

EXAMPLE 8

Expression of Recombinant Glycoprotein

Cells produced in Example 5 are transformed using a technique described supra with a recombinant expression vector which comprises DNA encoding a glycoprotein. The glycoprotein is expressed and is found to have intact carbohydrate side chains, sialic acid residues not having been cleaved.

This demonstrates the usefulness of the present invention for the production of recombinant glycoproteins with intact carbohydrate side chains.

What is claimed is:

1. A process for the production of a glycoprotein, comprising expressing a nucleic acid encoding the glycoprotein in a Chinese Hamster Ovary cell line, wherein a constitutive sialidase gene of the Chinese Hamster Ovary cell line is not functionally expressed.

2. A recombinant Chinese Hamster Ovary cell line comprising:

a nucleic acid sequence encoding a sialidase normally expressed constitutively in the recombinant Chinese Hamster Ovary cell line; wherein the nucleic acid sequence encoding the sialidase is not functionally expressed in the cell;

and an exogenous nucleic acid sequence encoding a glycoprotein.

3. A recombinant eukaryotic cell line wherein a constitutive sialidase gene of the cell line is not functionally expressed and wherein the cell line is Chinese Hamster Ovary cell line.

* * * * *